United States Patent [19]

Hazar

[11] 4,017,971

[45] Apr. 19, 1977

[54] MODULAR PROSTHETIC DENTURES

[75] Inventor: Mitchell M. Hazar, Phoenix, Ariz.

[73] Assignee: American Denture Corporation, Scottsdale, Ariz.

[22] Filed: Dec. 11, 1975

[21] Appl. No.: 639,982

[52] U.S. Cl. .................................................. 32/2
[51] Int. Cl.² ........................................ A61C 13/00
[58] Field of Search ........................................ 32/2

[56] References Cited

UNITED STATES PATENTS

| | | | |
|---|---|---|---|
| 2,464,987 | 3/1949 | Nelson | 32/2 |
| 2,685,133 | 8/1954 | Greene et al. | 32/2 |
| 2,776,485 | 1/1957 | Stuart | 32/2 |
| 3,083,459 | 4/1963 | McMurry et al. | 32/2 |
| 3,646,676 | 3/1972 | Mitchell | 32/2 |

Primary Examiner—G.E. McNeill

[57] ABSTRACT

The disclosure relates to modular prosthetic dentures comprising maxillary and mandibular units, each unit being fittable to a variety of patients; each unit having teeth fixed to a hard base on which a deflectably formable layer is deflectably fittable to an edentulus ridge; one of said units having a flat plane acclusion geometry and said mandibular unit having a retro-molar pad fitting extension ½ inch or more in length; said extension comprising deflectably formable material; the deflectably formable material of both denture units being adapted to be united with a hard liner forming material when in an uncured state and when impression formed in a patient's mouth.

6 Claims, 6 Drawing Figures

MODULAR PROSTHETIC DENTURES

PRIOR ART

The following prior art is hereby made of record and is believed to be most pertinent to the present invention. All of the following patents are United States Patents.

U.S. Pat. No. 3,083,459
U.S. Pat. No. 3,241,238
U.S. Pat. No. 3,464,111
U.S. Pat. No. 3,667,123
U.S. Pat. No. 3,727,309
U.S. Pat. No. 3,839,796

BACKGROUND OF THE INVENTION

Various prosthetic dentures have been produced by setting groups of individual teeth in hard base structures and final impression fitting of such hard base structures have been generally performed by inserting the hard base structure into the mouth of a patient with various impression taking materials and subsequently the impressions are utilized for producing a suitable recess adapted to fit an edentulus ridge of a patient from which the impression is taken.

Heretofore, impressions of a toothless gum area have been made and it has been common practice to produce hard base dentures in accordance with such impressions; however, due to the mass of material involved in producing a hard base denture, it has been difficult to allow such hard base material to cure in a person's mouth in an impression taking position, and thus costly and complex methods have always been resorted to in the production of a prosthetic denture. Many of the plastic materials which are hardenable are utilized for producing a prosthetic gum structure adjacent to prosthetic teeth and due to the structural mass requirements in the amount of plastic material to be cured in connection with the prosthetic teeth is such as to cause discomfort of a patient and thereby preventing the complete impression taking and curing of the hard base structure in a patient's mouth.

Additionally, the prior art has employed elastomeric material which is curable at low temperature in person's mouth for taking impressions therein, and many such materials are only intimately bondable to a like material but not readily bondable to a hard base plastic material such as an acrylic material or the like. Dentures produced in this manner have encountered functional difficulties hereinbefore described, in that the food particles are collected between the elastomeric material and the prosthetic teeth during mastication of food in the mouth of a person wearing such prior art prosthetic dentures.

Some prior art prosthetic dentures have been produced with hard rigid palate portions adapted to be placed adjacent the palatal vault of a person's mouth and due to the various configurations of person's mouths, these hard palate portions have been unsatisfactory since in many cases relatively thick liners have caused the hard palate area to become quite thick, which tends to create speech as well as mastication problems.

In addition to the foregoing prior art dental practice, many approaches have been made to the provision of a modular artificial denture which may be readily and easily fitted to a variety of patients and which may be satisfactory both as to occlusion and as to overall comfort.

Even though various modular artificial dentures have been produced and even though they have been centrically related as maxillary and mandibular sets, the cusp areas of the related maxillary and mandibular units have been unnatural to the particular patient and have caused occlusion excursions which have created temporo mandibular joint syndromes or spasms of the muscles of mastication. This problem has rendered the art of modular prosthetic dentures somewhat lacking in practical application. Any set of dentures, including a maxillary denture and a mandibular denture which is adapted to fit a variety of patients, will without exception have cusp occlusion areas which will be unnatural to some patients and eventually cause temporo mandibular joint syndrome.

Additionally, the mandibular units of prior art modular dentures have lacked proper support so as to remain in place for proper occlusion and for comfortable and reliable use.

SUMMARY OF THE INVENTION

The present invention relates to a novel modular prosthetic denture and a method for producing such dentures. The invention comprises an assembly of individual teeth or an assembly of integral cast prosthetic teeth which are bonded at their root simulating areas to a hard base structure such as a compatible acrylic which will bond intimately to the teeth, which may be of like material, and a deflectably formable layer on the hard base layer provides for a recess adapted generally to conform to edentulus ridge areas of a patient, and deflectably formable layer is bonded to the hard base acrylic or other material so that a complete artificial denture, according to the invention, may be finally fitted to the patient's mouth by heating the deflectably formable material for the final impression fitting within the mouth.

In accordance with the present invention, modular prosthetic dentures are produced in pairs comprising maxillary and mandibular units and at least one of these units is provided with flat plane occlusion geometry so as to permit a variety of patients to be fitted with the modular denture and so as to avoid the temporo mandibular joint syndrome condition which has plagued the prior art use of modular dentures wherein any given modular denture may be used to fit a variety of patients. The flat plane occlusion geometry may be provided on the occlusion surface area of either the maxillary or mandibular denture unit and the other of the units of each set may have cusp geometry if desired so as to provide desired mastication characteristics. Thus, the invention permits occlusion on a flat plane of at least one of said denture units of the invention and thereby allows antero-posterior and lateral excursions of the denture units relative to each other and such excursions may be performed with such freedom as to avoid the temporo mandibular joint syndrome which has been so common to the use of prior art modular dentures. Additionally, the invention comprises a mandibular unit cooperating with the aforementioned maxillary unit and this mandibular unit is provided with retro-molar pad extensions ranging between ½ inch and 1 inch to a maximum of approximately 1¼ inch so as to obtain reliable support of the mandibular denture relative to the maxillary denture so that proper occlusion is insured due to efficient suppport of the mandibular denture in its proper location at all times so as to cooperate with the maxillary denture and further to cooperate in flat plane occlusion as provided by the flat plane occlusion geometry of one of said denture units, as hereinbefore described.

Another species of the invention comprises an assembly of integral cast prosthetic teeth having a hard base structure bonded to the upper portions thereof and having a first layer of deflectably formable material formed generally to fit an edentulus ridge area of a patient and a second layer overlayer the deflectably formable layer, the second layer when cured being a hard plastic bondable to the deflectably formable material, and this hard plastic, being quite thin, is subject to taking of an impression in a person's mouth of that person's edentulus ridge area while the second layer is in soft condition, but activated to become hardened, and the peripheral areas of the second layer bond to the first deflectably formable layer.

The preferred embodiment of the invention comprises a prosthetic denture having a hard base bonded to an assembly of prosthetic teeth, and the hard base carries a soft palate which includes a soft layer of deflectably formable material adapted generally to fit the upper edentulus ridge area of a patient, and the soft palate being of deflectably formable material is capable of heated and/or deflectably formed within the patient's mouth, subsequent to which a hard liner forming material is cast on the soft palate within the person's mouth to provide a relatively thin hard palate in the palatal vault of the patient.

The preferred embodiment of the invention also comprises the production of several sizes of prosthetic dentures which include an assembly of prosthetic teeth bonded to a hard base structure and whereon a soft deflectable layer is also bonded to the hard base so that the soft deflectable layer may initially be deflectably formed in a person's mouth generally to fit the features of an edentulus ridge area of the patient, whereupon a hard liner may subsequently be cast in the deflectably formed soft layer and the hard liner is impression formed to precisely fit the respective edentulus ridge area of the patient's mouth.

The preferred method of the invention comprises the casting of a hard base prosthetic gum structure about an assembly of prosthetic teeth such that the prosthetic teeth are rigidly bonded to the hard base prosthetic gum structure, then a soft deflectably formable layer is cast on the hard base gum structure so as generally to conform to a human edentulus ridge area whereupon the soft layer of material may be deflectably formed in a person's mouth to a set condition so as to quite closely conform to the edentulus ridge area in the patient's mouth. In order to deflectably form the soft layer it may be heated slightly, as in hot water, so that it may readily be deflected into conformance with the features of the edentulus ridge area in the patient's mouth, whereupon the soft layer may then be cooled and hardenable acrylic or other suitable material may be placed on the deflectably formed soft layer and then reinserted into the patient's mouth and left until the last mentioned layer of material has hardened into a hard, rigid structure exactly conforming to the edentulus ridge area of the patient's mouth.

Accordingly, it is an object of the invention to provide very economical modular prosthetic dentures and methods for economically producing the same, and accurately fitting the denture to the edentulus ridge of a human patient.

Another object of the invention is to provide modular dentures comprising maxillary and manibular units cooperating as a set wherein one of said units is provided with flat plane occlusion geometry so as to avoid temporo mandibular joint syndrome or spasms of the muscles of mastication, heretofore prevalent in the use of many artificial modular dentures.

Another object of the invention is to provide modular dentures comprising maxillary and mandibular units, one of which has flat plane occlusion geometry, and wherein retro-molar pad extensions are integral with the mandibular unit. These extensions extend for a distance of ½ inch or more so as to provide an efficient sealed and fitted support of the mandibular denture on the mandible of the patient so as to maintain the mandibular unit in proper position to cooperate with the flat plane occlusion between the two dentures and to afford accurate antero, posterior and lateral excursions and thereby provide for efficient mastication as well as the avoidance of temporo mandibular joint syndrome, as hereinbefore set forth.

Another object of the invention is to provide a method for producing prosthetic dentures wherein a hard base prosthetic gum structure is bonded to an assembly of prosthetic teeth; a soft layer is bonded to the hard base and is of delectably formable material subject to thermal setting action or the like and whereby the deflectably formable layer is located in a person's mouth and deflected into close fitting relation with an edentulus ridge area thereof and is then cooled and hardenable material is placed on the soft layer and reinserted in the mouth and allowed to cure into a hard impression fitted liner.

Further objects and advantages of the invention may be apparent from the following specification, appended claims and accompanying drawings.

DESCRIPTION OF THE PREFERRED EMBODIMENTS

Figure 1:
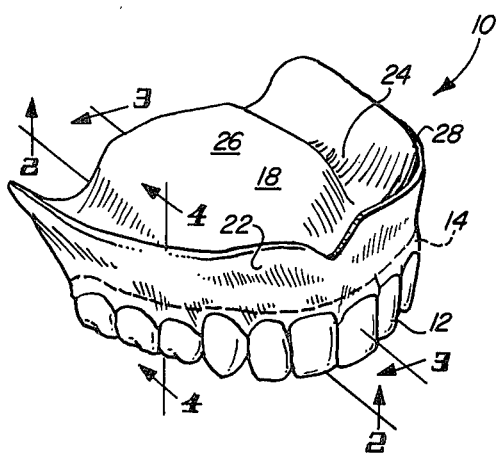
FIG. 1 is a prspective view of a modular maxillary denture unit in accordance with the present invention.
Figure 4:
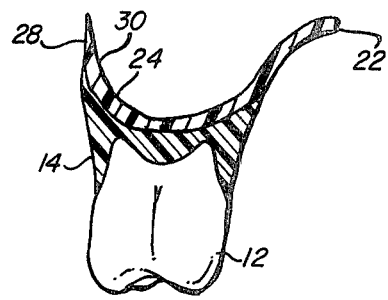
FIG. 4 is a sectional view taken from the line 4—4 of FIG. 1.
Figure 2:
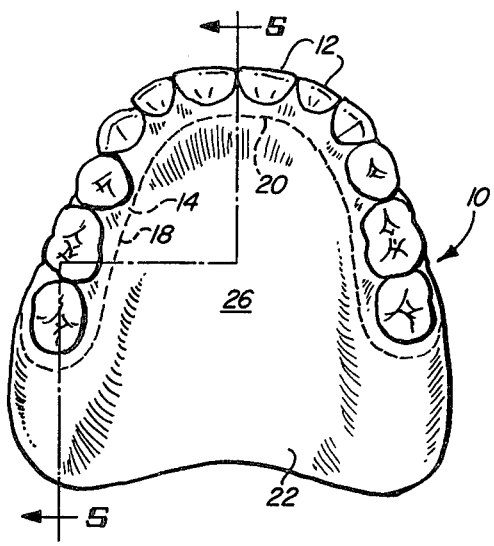
FIG. 2 is a bottom view of the denture unit shown in FIG. 1.
Figure 5:
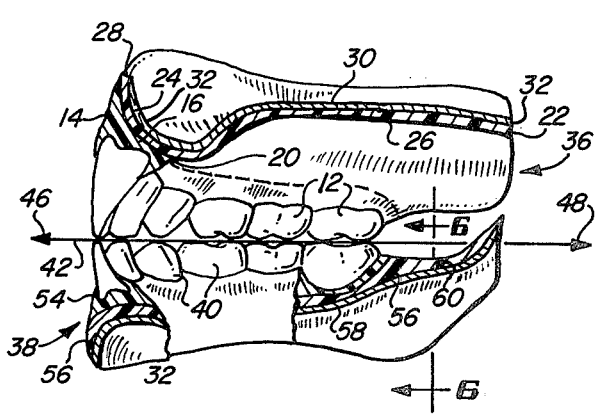
FIG. 5 is a vertical sectional view taken of modular denture units including a maxillary unit and a mandibular unit and showing, by a straight line, flat plane occlusion geometry of one of the units and also showing portions broken away and in sections to amplify the illustration.
Figure 3:
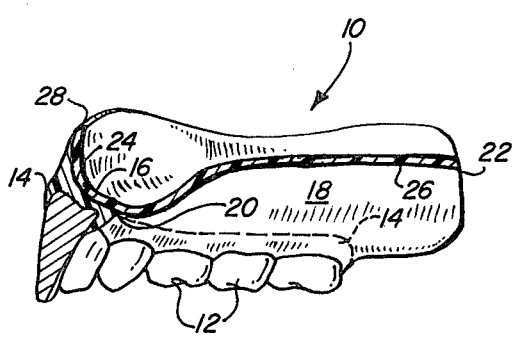
FIG. 3 is a sectional view taken from the line 3—3 of FIG. 1.

The preferred embodiment of the invention comprises modular prosthetic dentures such as shown in FIG. 1 and 5 of the drawings. A maxillary prosthetic denture, shown in FIG. 1, is designated generally 10 and as shown in FIGS. 2 and 3, an assembly of prosthetic teeth 12 are cast into and bonded to a hard base structure 14. The prosthetic teeth 12 and the hard base structure 14 are preferably of an acrylic material such as manufactured by Coe Laboratories, Inc., Chicago, Ill. 60658. Also, this hard base material may be such as manufactured by Cosmos Dental Products, Inc., 4330 22nd Street, Long Island City, N.Y. Thus, the preferred form of the invention includes a hard base prosthetic gum structure 14 to which are bonded an assembly of prosthetic teeth 12 and this hard base and assembly may be molded in a conventional manner as disclosed in U.S. Pat. No. 3,839,796 and as shown in FIG. 3 wherein a generally U-shaped recess 16 is formed generally to correspond and coextend with an edentulus ridge area of a patient. As shown in FIGS. 1, 2 and 3, the central area 18 of the hard base 14 is generally open and is provided with a terminus 20 located a short distance behind the incisor or front teeth and thus the hard base 14 is generally U-shaped, all as shown best in FIGS. 1 and 2.

Bonded to the hard base 14 is a soft deflectable layer 22 and this layer 22 is made of material compatible with the material of the hard base 14 and preferably of deflectably formable acrylic material such as the "Super Soft" acrylic manufactured by Coe Laboratories, Inc., hereinbefore referred to. Additionally, such soft deflectable material is manufactured by William Getz Corporation, Chicago, Ill.

Accordingly, the soft layer 22 is bonded to the U-shaped recess 16 of the hard base 14 and the soft layer 22 is provided with a U-shaped recess 24 which is adapted generally to fit an edentulus ridge area of a patient and is generally coextensive with the assembly of prosthetic teeth 12. The soft layer 22 is provided with a palatal vault palate portion 26 which abridges the open area of the hard base 14, all as shown best in FIGS. 1, 2 and 3. The soft layer 22 is provided with a rim 28 generally surrounding the recess 16 and the denture as shown in FIGS. 1, 2 and 3 may be produced in a variety of sizes such that the recess 16 may generally fit various patients.

Figure 6:
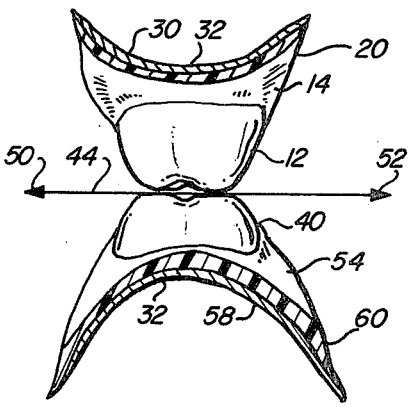
FIG. 6 is a sectional view taken from the line 6—6 of FIG. 5, showing flat plane occlusion geometry of one of the denture units and illustrating flat plane or lateral excursion freedom of the dentures relative to each other.

In accordance with the method of the invention, this denture as shown in FIGS. 1, 2 and 3 may be fitted to a patient's mouth as follows, and the structure may be completed as shown in FIGS. 1, 2 and 3, in the following manner and in accordance with the method of the invention:

An artificial denture, such as shown in FIG. 3 of the appropriate size, generally to fit a patient's edentulus ridge, is selected and the hard base 14, together with the soft liner 20, may first be heated to permit lateral spreading or compression to conform to the lateral spacing of a patient's edentulus ridges, then the soft layer 22 which is deflectably formable is heated in hot water or the like to render it readily pliable and thermally settable. The denture is then placed in the patient's mouth and the rim 28 of the soft layer 22 is deflectably formed into close conformance with the edentulus ridge area of the patient while the palatal vault palate portion 26 is formed upwardly into intimate contact with the palatal vault of the patient's mouth, and then the denture is removed and the soft layer 22 is chilled and a hard liner material designated 30 in FIGS. 5 and 6 is placed on the soft layer 22. This material 30 is similar to the hard acrylic material of the hard base 14 and is initially placed on the soft layer in uncured form such that it is substantially fluid in condition. The denture is then placed in the patient's mouth to impression form the hard liner 30 to provide a generally U-shaped recess 32 which exactly conforms as an impression fitting to the edentulus ridge area of the patient, and this hard liner 30 is then allowed to harden and cure into exact conformance with the edentulus ridge area.

Accordingly, the liner 30 is very thin at the palatal vault area 26 due to the fact that the portion 26 of the soft layer 22 was previously formed into close intimate contact with the palatal vault of the patient's mouth, and thus the hard liner 30 may be very thin, yet rigid and bonded to the palatal vault or hard palate portion 26 of the soft layer 22.

It will be appreciated that the soft layer 22 may have characteristics which allow it gradually to harden over a period of several days or a month, such that it eventually becomes quite hard and comparable to that of the hard base 14 and the hard liner 30.

It will be appreciated that the structure of the invention and the method hereinbefore recited provides substantial advantage in fitting the palatal vault of the patient's mouth due to the fact that the hard base 14 is open in the middle portion of the upper prosthetic denture, all as indicated at 18 in FIGS. 1 and 2 of the drawings, and the soft layer 22 abridges this opening rearward of the terminus 20 so that the palatal vault area of the mouth may readily be fitted by deflecting the soft deflectably formable material of the layer 22 into close conformity with the palatal vault and the thickness of the material of the soft layer at this point may be nominal, and also the thickness of the hard liner 30 may be nominal thereafter due to the fact that the soft layer has been previously deflectably formed into close conformity with the features of the patient's mouth.

It will be appreciated that the hard liner 30 is of material, as for example such material as made by the Coe Laboratories hereinbefore referred to, and the product is known as "Coe-Rect". This is a rigid denture liner known to the dental profession. Also, the Cosmos company, hereinbefore referred to, produces a methyl methacrylate base material and these materials are all generally acrylic so that they are compatible in chemistry to efficient bonding to each other. The soft material of the soft layer 22 being deflectably formable at temperatures ranging between body temperature and 160°, may be suitably heated to a comfortable degree for impression forming in the person's mouth, as hereinbefore described, preliminary to the casting and impression forming of the hard liner 30 on the soft layer 22.

As shown in FIG. 5 of the drawings, the modular artificial dentures of the invention comprise the maxillary unit generally indicated at 36 and also a mandibular modular denture unit generally indicated at 38. The mandibular denture unit is provided with artificial teeth 40 which have flat plane occlusion geometry as indicated by a straight line 42 in FIG. 5 and by straight lines 44 in FIG. 6, and it will be understood that the flat plane occlusion geometry may be provided on either the teeth 40 or the teeth 12 of the maxillary denture 36. The teeth 12, however, have been shown with cusp portions, as an example, and these cusp portions may be provided on either the teeth 12 or the teeth 40 if desired, except that at least one of the sets of teeth must have flat plane occlusion geometry, as indicated by the straight lines 42 and 44, so as to provide for complete freedom of antero excursions of the dentures relative to each other, as indicated by an arrow 46 and also to provide complete excursion freedom in the posterior direction, as indicated by the arrow 48. Additionally, the flat plane occlusion geometry, as hereinbefore described, provides for complete freedom of lateral occlusion excursions in the directions of the arrows 50 and 52 shown in FIG. 6 of the drawings. Accordingly, it will be appreciated by those skilled in the art that flat plane occlusion geometry such as disclosed in FIGS. 5 and 6 may be provided by arranging the flat plane geometry on the teeth 12 or 40 of either of the dentures 36 or 38. Additionally, it will be understood that flat plane occlusion geometry may be provided on both sets of teeth 12 and 40 if desired. This flat plane occlusion geometry in combination with a modular denture provides for the ultimate economy in artificial dentures which may be fitted to a variety of patients whose occlusion characteristics have been different from each other and whose occlusion characteristics have become such a habit that a change in occlusion geometry could cause the aforementioned temporo mandibular joint syndrome or spasms of the muscles of mastication. Accordingly, the combination of modular dentures which are provided with soft portions deflectably fitted to various patients and the flat plane occlusion geometry permits the successful fitting of a modular denture to a variety of patients and the ultimate of comfort and occlusion efficiency for anyone of several patients to which a given set of modular dentures may be fitted in accordance with the present invention. With reference to FIG. 5 it will be seen that the mandibular denture is provided with a hard base 54 similar to the hard base 14 of the maxillary denture 36 and bonded to the hard base 54 is a soft layer 56 generally corresponding in structure and function to the soft layer 22 hereinbefore described. The denture ultimately is also provided with a hard liner 58 which is bonded to the soft layer 56 in a similar manner to that of the hard liner 30 hereinbefore described.

At the rearward portion of the mandibular denture 38, are retro-molar pad fitting extensions 60, one on each side of the denture and these extensions 60 are continuations of the soft layer 56 which is deflectably formable so that these portions 60 may be heated in the manner hereinbefore described and formed to fit the retro-molar pad of the particular patient at each side of the mandible. Whereupon, the hard liner 58 may be bonded thereto in the manner as hereinbefore described in connection with the hard liner 30.

The retro-molar extension 60 extends ½ inch or more beyond the edentulus ridge area and engages the mucus membrane on which a proper and efficient seal may be made to efficiently hold the mandibular denture 38 in place and to thereby allow it to cooperate with the maxillary denture and in firm and efficient position to cooperate with the flat plane occlusion geometry and to provide for efficient holding and mastication operation of the dentures relative to each other. It will be appreciated that the retro-molar pad extension 60 extends ½ inch or more, usually ranging between ½ inch and in some instances may be 1¼ inches long if desired.

The modular denture produced for the profession will be produced with the extension 60 somewhat longer than needed so that this extension may be trimmed to accomodate various patients preliminary to the heating and fitting of these retro-molar fitting pad areas 60 to the particular patient.

In accordance with the foregoing, it will be appreciated that the modular denture of the invention may be produced and fitted as set forth herein and that the combination of the deflectably formable layer 22 for initial impression fitting and the hard liner 30 together with flat plane occlusion and the retro-molar pad extensions provides for the efficient fitting and use of modular dentures to afford efficient mastication as well as ultimate comfort of the patient and to provide modular artificial dentures which may be produced in a few sizes to accomodate all prospective patients and that each size may be used to fit a great variety of patients without causing some of the previous problems hereinbefore referred to.

It will be obvious to those skilled in the art that various modifications may be resorted to without departing from the spirit of the invention.

I claim:

1. Modular prosthetic dentures comprising maxillary and mandibular units; each unit being fittable to a variety of patients; each unit having a hard base; teeth fixed to said hard base; a deflectably formable layer bonded to said hard base and being deflectably fittable to an edentulus ridge; the teeth of one of said units having flat plane occlusion geometry.

2. The invention as defined in claim 1, wherein: said mandibular unit is provided with retro-molar pad fitting extensions ½ inch or more in length; said extensions comprising deflectably formable material; the deflectably formable material of both denture units being adapted to be united with a hard liner forming material when in an uncured state and when impression formed in a patient's mouth.

3. Modular prosthetic dentures comprising maxillary and mandibular units; each unit being fittable to a variety of patients; each unit having a hard base; teeth fixed to said hard base; a deflectably formable layer bonded to said hard base and being deflectably fittable to an edentulus ridge; said teeth of one of said units having a retro-molar pad fitting extension ½ inch or more in length; said extension comprising deflectably formable material; the deflectably formable material of both denture units being adapted to be united with a hard liner forming material when in an uncured state and when impression formed in a patient's mouth.

4. The invention as defined in claim 3, wherein: said retro-molar pad fitting extension ranges in length between ½ inch and 1¼ inches.

5. Modular prosthetic dentures comprising maxillary and mandibular units; each unit being fittable to a variety of patients; each unit having a hard base; teeth fixed to said hard base; a deflectably formable layer bonded to said hard base and being deflectably fittable to an edentulus ridge; said teeth of one of said units having flat plane occlusion geometry; said mandibular units having a retro-molar pad fitting extension ½ inch or more in length; said extension comprising deflectably formable material; the deflectably formable material of both denture units having a hard liner adapted intimately to fit respective edentulus ridges of a patient's mouth.

6. The invention as defined in claim 5, wherein: said hard liner of said mandibular unit covers an upper area of said retro-molar pad fitting extension.

* * * * *